US010800721B1

(12) United States Patent
Wang et al.

(10) Patent No.: US 10,800,721 B1
(45) Date of Patent: Oct. 13, 2020

(54) METHOD FOR PREPARING 2-CYCLOHEXYL CYCLOHEXANOL

(71) Applicant: CHINA PETROCHEMICAL DEVELOPMENT CORPORATION, Kaohsiung (TW)

(72) Inventors: Yi-Chi Wang, Kaohsiung (TW); Hsin-Wei Chang, Kaohsiung (TW); Weng-Keong Tang, Kaohsiung (TW); Chia-Hui Shen, Kaohsiung (TW)

(73) Assignee: CHINA PETROCHEMICAL DEVELOPMENT CORPORATION, Kaohsiung (TW)

( * ) Notice: Subject to any disclaimer, the term of this patent is extended or adjusted under 35 U.S.C. 154(b) by 0 days.

(21) Appl. No.: 16/783,672

(22) Filed: Feb. 6, 2020

(30) Foreign Application Priority Data

Jul. 22, 2019 (TW) .............................. 108125835 A

(51) Int. Cl.
*C07C 29/00* (2006.01)
*B01J 21/00* (2006.01)
*C07C 29/145* (2006.01)
*B01J 21/04* (2006.01)
*B01J 21/08* (2006.01)
*B01J 21/18* (2006.01)
*B01J 23/42* (2006.01)
*B01J 37/08* (2006.01)
*B01J 23/755* (2006.01)
*B01J 23/75* (2006.01)
*B01J 37/02* (2006.01)
*B01J 23/46* (2006.01)

(52) U.S. Cl.
CPC ............. *C07C 29/145* (2013.01); *B01J 21/04* (2013.01); *B01J 21/08* (2013.01); *B01J 21/18* (2013.01); *B01J 23/42* (2013.01); *B01J 23/462* (2013.01); *B01J 23/75* (2013.01); *B01J 23/755* (2013.01); *B01J 37/0219* (2013.01); *B01J 37/0236* (2013.01); *B01J 37/088* (2013.01)

(58) Field of Classification Search
CPC .................................................... C07C 29/145
See application file for complete search history.

(56) References Cited

U.S. PATENT DOCUMENTS

| 4,002,693 A | * | 1/1977 | King | ....................... C07C 37/07 568/747 |
| 5,756,863 A | * | 5/1998 | Murayama | ............ C07C 29/145 568/814 |
| 8,519,192 B2 | * | 8/2013 | Ma | ......................... B01J 27/053 568/338 |

OTHER PUBLICATIONS

Felfoldi et al. Sonochemical hydrosilylation of 2-substituted cyclohexanones in the presence of Wilkinson complex. Ultrasonic Sonochemistry, vol. 7, 15-17. (Year: 2000).*

* cited by examiner

*Primary Examiner* — Sirarl A Witherspoon
(74) *Attorney, Agent, or Firm* — Kelly & Kelley, LLP

(57) ABSTRACT

Provided is a method for preparing 2-cyclohexyl cyclohexanol, including: hydrogenating a cyclohexanone dimer with hydrogen gas at a temperature ranging from 150 to 250° C. in a reactor containing a catalyst to prepare 2-cyclohexyl-cyclohexanol, wherein the molar ratio of the hydrogen gas and oil ranges from 1 to 25. The method has advantages of high yield properties and allows for mass production, thereby enhancing the value of the industrial application.

18 Claims, No Drawings

METHOD FOR PREPARING 2-CYCLOHEXYL CYCLOHEXANOL

1. TECHNICAL FIELD

The present disclosure relates to methods for preparing 2-cyclohexyl cyclohexanol, and particularly, to a method for preparing 2-cyclohexyl cyclohexanol by hydrogenating a cyclohexanone dimer under relative mild conditions.

2. DESCRIPTION OF THE PRIOR ART

2-Cyclohexyl cyclohexanol, a chemical substance with a high boiling point, can be used as an intermediate of material synthesis, in addition to being used as a chemical reagent, a solvent and a fine chemical in a various applications, including medical, chemical engineering, coating and solar industries, and is thus a chemical substance with values.

Cyclohexanol-based compounds can be prepared primarily from a phenol hydrogenation process, a cyclohexene hydration process and a cyclohexane oxidation process, among which the cyclohexane oxidation process has shortcomings of low selectivity, low conversion rate and high energy consumption and having a great safety risk of during the oxidation preparation procedure thereof; while the cyclohexene hydration process has problems of low reaction rate, low equilibrium conversion. By contrast, the phenol hydrogenation process has the properties of high purity of product, stable reaction and so on, and is likely to be recommended and applied in an industrial production.

However, the selection and operation on the processes in response to different structures of cyclohexanol-based compounds can be substantially different due to the differences in structures and properties between the reactants and/or products, especially for the preparation of 2-cyclohexyl cyclohexanol. There still exists the need to provide a method for preparing 2-cylcohexyl cyclohexanol which gives a high yield and is suitable for scale production.

SUMMARY

The present disclosure provides a method for preparing 2-cyclohexyl cyclohexanol, including hydrogenating a cyclohexanone dimer of Formula (I) with hydrogen gas at a temperature ranging from 150 to 250° C. in a reactor containing a catalyst to prepare the 2-cyclohexyl cyclohexanol,

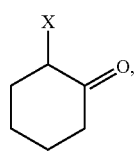

(I)

wherein X is cyclohexyl, cyclohexylidene, cyclohexenyl or unsubstituted phenyl, and wherein the molar ratio of the hydrogen gas to oil ranges from 1 to 25.

In one embodiment of the method of the present disclosure, the cyclohexanone dimer of Formula (I) is prepared by self-condensation of cyclohexanone. In another embodiment, the cyclohexanone dimer of Formula (I) is 2-(1-cyclohexenyl)cyclohexanone.

In one embodiment of the method of the present disclosure, the catalyst includes an active metal selected from at least one of Group VIIIB metals and a carrier, wherein the active metal can be at least one selected from the group consisting of platinum, iron, cobalt, nickel, ruthenium, rhodium, palladium, osmium and iridium. In another embodiment, the carrier is at least one selected from the group consisting of alumina, silica and carbon. In still another embodiment, the active metal includes 0.1 to 10 wt % of the weight of the catalyst.

In one embodiment of the method of the present disclosure, the cyclohexanone dimer of Formula (I) is hydrogenated under a pressure condition of 5 to 80 bars.

In one embodiment of the method of the present disclosure, the reactor is a continuous reactor. In another embodiment, the continuous reactor is a fixed bed reactor.

In one embodiment of the method of the present disclosure, when the reactor is a continuous reactor such as a fixed bed reactor, the hydrogenation temperature is from 150 to 250° C., wherein the weight hourly space velocity (WHSV) of the cyclohexanone dimer is from 0.1 to 10 hr$^{-1}$. In another embodiment, the cyclohexanone dimer flows in the same direction as the hydrogen gas in the fixed bed reactor.

In order for the reactant stream to rapidly equilibrate to the reaction temperature during the reaction, the cyclohexanone dimer and the hydrogen gas are heated respectively prior to being fed into the reactor in the present disclosure, so as to prevent the large temperature difference between the reactant stream and the reactor when the reactant stream enters the reactor, which results in an influence on reactivity of the reactant. In one embodiment of the method of the present disclosure, when the reactor is a fixed bed reactor and the hydrogenation is performed at a temperature from 150 to 250° C., the method further includes a step of heating both the hydrogen gas and the cyclohexanone dimer to a temperature of from 150 to 250° C., while controlling the pressure to be within a range of 5 to 80 bars.

In one embodiment of the method of the present disclosure, when the reactor is a continuous reactor, the method further includes a step of mixing the cyclohexanone dimer and the hydrogen gas in a mixing tank upstream to the continuous reactor, wherein the mixing tank is operated at 150 to 250° C. under a pressure of 5 to 80 bars.

In one embodiment of the method of the present disclosure, the reactor is a batch reactor.

In one embodiment of the method of the present disclosure, when the reactor is a batch reactor, the mass ratio of the catalyst to the cyclohexanone dimer is from 2 to 20%. In another embodiment, the batch reactor further includes an agitator device, and the agitator device rotates at a speed of 250 to 500 rpm during the hydrogenation. In the embodiment in which the reactor is a batch reactor, the hydrogenation is performed at a temperature of 150 to 250° C. for 4 to 8 hrs.

In one embodiment, the method of the present disclosure further includes a step of separating the 2-cyclohexyl cyclohexanol from hydrogen gas and byproducts with a separation unit downstream to the reactor.

In one embodiment of the method of the present disclosure, the conversion rate of the hydrogenation is from 70 to 100%. In another embodiment, the selectivity of the hydrogenation is from 5 to 100%.

The method for preparing 2-cyclohexyl cyclohexanol described in the present disclosure is performed through hydrogenation of cyclohexanone dimer at particular ranges of temperature and pressures in the presence of a catalyst, so as to prepare 2-cyclohexyl cyclohexanol with a yield effectively improved by 50% or higher. Moreover, the resultant product needs no separation through a complex purification procedure, since the preparation process has the nature of high conversion rate and selectivity. The preparation cost is thus reduced, and the method has the value of the industrial application.

DETAILED DESCRIPTION OF THE EMBODIMENTS

The implementing modes of the present disclosure are illustrated by following specific embodiments, and any one skilled in the art can easily realize the advantages and effects of the present disclosure based on the content described in the description. The present disclosure also can be performed or applied by other different implementing modes, and the details of the present disclosure each can be modified an altered differently without departing from the scope of the present disclosure, based on different views and applications. Furthermore, all of the ranges and values recited in the present disclosure are inclusive and combinable. Any numerical value or point, such as any integers, fallen within the ranges recited herein can be used as the lower or upper limit to derive a subrange.

According to the present disclosure, a method for preparing 2-cyclohexyl cyclohexanol includes the steps of: hydrogenating a cyclohexanone dimer of Formula (I) with hydrogen gas a temperature ranging from 150 to 250° C. in a reactor containing a catalyst at to prepare 2-cyclohexyl cyclohexanol; wherein the molar ratio of the hydrogen gas to oil is 1 to 25.

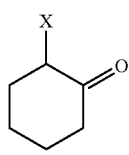

(I)

wherein X is cyclohexyl, cyclohexylidene, cyclohexenyl or unsubstituted phenyl.

In some embodiments, the ratio of hydrogen to oil is 1, 2, 3, 4, 5, 6, 7, 8, 9, 10, 11, 12, 13, 14, 15, 16, 17, 18, 19, 20, 22, 22, 23, 24, or 25, and even more specific in the range of, such as 5, 12.1, and 18.2.

In the present disclosure, "the ratio of hydrogen to oil" refers to the molar ratio of hydrogen gas to the reactant in the reactor, i.e., the molar ratio of hydrogen gas to the cyclohexanone dimer of Formula (I).

The cyclohexanone dimer of Formula (I) is not limited to the product of the reaction using cyclohexanone as a raw material, and can be derived from any one of the suitable sources such as dianon, the byproduct isolated from the waste oil (X oil) resulting from a caprolactam process (see the study reported in V. A. Pozdeev et al., Zhurnal Prikladnoi Khimii, 2011, 84(4)).

In one embodiment, the cyclohexanone dimer of Formula (I) is prepared by self-condensation of cyclohexanone, wherein the self-condensation of cyclohexanone is performed by allowing cyclohexanone molecules to react with each other in the presence of an acid or a base catalyst, with the Reaction Scheme being shown below:

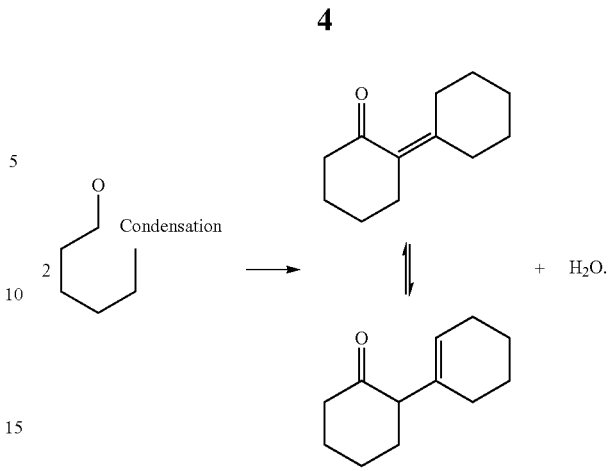

The above self-condensation of cyclohexanone generally produces two resonance isomers, namely, 2-(1-cyclohexenyl)cyclohexanone and 2-(cyclohexylidene)cyclohexanone, respectively.

For the process of preparing a cyclohexanone dimer by self-condensation of cyclohexanone, patents such as U.S. Pat. Nos. 4,002,693, 3,980,716, 3,880,930 and CN101205170 and documents such as Shanxi coal chemical research institute, Chinese academy of sciences, FINE CHEMICALS, 1994, 11(5) can be taken for reference, the contents of which are incorporated herein by reference in their entireties. Optionally, the method for preparing 2-cyclohexyl cyclohexanol of the present disclosure can be integrated with the above process for cyclohexanone dimer.

In another embodiment, the cyclohexanone dimer of Formula (I) is 2-(1-cyclohexenyl)cyclohexanone. For the preparation methods of 2-(1-cyclohexenyl)cyclohexanone, TW201226379 can be taken for reference, the content of which is also incorporated herein in its entirety.

The hydrogen gas includes undiluted hydrogen gas, and diluted hydrogen gas containing inert carrier gas, wherein the inert carrier gas can be selected from nitrogen, argon, helium or neon gas. In one embodiment, the diluted hydrogen gas containing inert carrier gas includes 10% or more hydrogen gas, such as, 10%, 15%, 20%, 25%, 30%, 40%, 45%, 50%, 55%, 60%, 65%, 70%, 75%, 80%, 85%, 90%, or 95% or more hydrogen gas, even includes pure hydrogen gas.

The hydrogenation takes place in the presence of a catalyst, wherein the catalyst includes an active metal having the hydrogenating function loaded on a carrier, and can be in a form including a porous catalyst.

In order to accelerate progress of the hydrogenation, the active metal is allowed to distribute preferentially on the outer surface of the catalyst, i.e., the outer surface of the carrier. In other words, the active metal on the surface layer of the catalyst has a concentration higher than that in the core. Thus, the overall load of the active metal and the production cost thereof are reduced, and the probability of diffusion of the reactant from the active catalyst surface to the core is also lowered. In one embodiment, the surface layer of the catalyst has high adsorption affinity to the cyclohexanone dimer of Formula (I), thereby enhancing the selectivity of the process effectively.

The active metal is at least one selected from Group VIIIB metals, wherein the active metal can be at least one element selected from the group consisting of platinum, iron, cobalt, nickel, ruthenium, rhodium, palladium, osmium and iridium. In the examples of the present disclosure, the active metal includes 0.1 to 10 wt %, and more specifically, the weight percent can be 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5 wt %, based on the weight of the catalyst.

The carrier of the catalyst is at least one selected from the group consisting of alumina, silica and carbon.

In preparation of the catalyst, the catalyst is obtained by loading the active metal on the carrier firstly, and then subjecting to washing, water removal and calcining treatments. In one embodiment, the preparation process of the catalyst further includes activating via a reduction treatment, with that the catalyst load being subjected to the activation procedure of the catalyst in the reactor being preferred.

Hydrogenation can be carried out in the presence or absence of an inert solvent. In one embodiment, the inert solvent is alcohols.

The reaction condition of hydrogenation includes a temperature of 150 to 250° C. and a pressure ranging from 5 to 80 bars. For example, the reaction temperature is 150, 155, 160, 165, 170, 175, 180, 185, 190, 195, 200, 205, 210, 215, 220, 225, 230, 235, 240, 245, 250° C.; and the pressure is 5, 10, 15, 20, 25, 30, 35, 40, 45, 50, 55, 60, 65, 70, 75, 80 bars. In the examples of the present disclosure, the reaction condition of hydrogenation including a temperature of 160 to 220° C. and a pressure ranging from 10 to 50 bars is particularly preferred.

The preparation method of the present disclosure can be applied in a batch process and a continuous process.

In a continuous process, the reactor is a continuous reactor operated by continuous feeding, continuous reaction and continuous discharging, and the continuous reactor includes a fixed bed reactor, a moving bed reactor, a fluidized bed reactor or a continuous stirring tank reactor. In the examples of the present disclosure, the continuous reactor is particularly preferably a fixed bed reactor.

The fixed bed reactor, also called packed bed reactor, is a reactor packed with a solid catalyst or a solid reactant to realize a multi-phase reaction process. In a fixed bed reactor, there is a bed layer which is stacked by the solid and is fixed during the reaction to allow a fluid to pass therethrough for reaction. Such a device is characterized in low wear loss of the catalyst and a relative higher yield can be achieved by using a small amount of catalyst, thereby facilitating reaching of a higher selectivity and a higher conversion rate.

In the present disclosure, the fixed bed reactor can be selected based on its actual requirement for heat transfer and the flowing direction of reactant, for example, trickle bed reactor, thermal insulation fixed bed reactor, heat exchange fixed bed reactor, axial flow fixed-bed reactor or radial flow fixed-bed reactor, but not limited thereto. An effect of high reaction rate can be reached when the reactant stream flows in a mode capable of utilizing all available surface area of the catalyst packed.

The fixed bed reactor can be operated in a mode that the reactant stream flows upwards or downwards, wherein the downwards flowing mode can enhance the interfacial area for delivery of hydrogen gas and contributes to a closer contact of the gas phase with the catalyst surface.

The flowing directions of reactant streams can be the same or opposite to each other. A significantly altered pressure difference occurs on the bed layer containing the catalyst, which impacts the efficiency and yield of the reaction, should be avoided. In one Example of the present disclosure, the reactant stream containing the cyclohexanone dimer flows in the same direction as that the hydrogen gas stream in the reactor, i.e., the above two reactant streams are allowed to pass through the bed layer packed with the catalyst.

Additionally, in the above fixed bed reactor, the catalyst can be packed in granular, network, honeycomb-like or fibril form, wherein the catalyst can be combined with an inert material, to regulate the pressure drop during the reactant flows through the bed layer containing the catalyst, to control the time period when the reactants contact the catalyst, and to pack the catalyst uniformly and dispersedly in the reactor. Therefore, the thermal energy generated during the reaction process is dissipated rapidly which contributes to temperature control during the reaction process.

In one embodiment, when the reactor is a fixed bed reactor, the hydrogenation is performed at a temperature of from 150 to 250° C., such as 150, 155, 160, 165, 170, 175, 180, 185, 190, 195, 200, 205, 210, 215, 220, 225, 230, 235, 240, 245, 250° C., and preferably 160 to 220° C. However, the hydrogenation should be performed at a temperature not more than 250° C. to avoid over-reaction which results in a relative low selectivity of reaction.

Since the continuous reactor of the present disclosure is classified to a heterogeneous reaction system, the flow rate of the reactant stream could affect flow layer thickness on the catalyst and the mass delivery between reactants. In one embodiment, the weight hourly space velocity (WHSV) of the cyclohexanone dimer is 0.1 to 10 $hr^{-1}$, such as 0.1, 0.2, 0.3, 0.4, 0.5, 0.6, 0.7, 0.8, 0.9, 1, 2, 3, 4, 5, 6, 7, 8, 9, 10 $hr^{-1}$.

In order to maintain a stable operation environment in the reactor, the method further comprises heating the hydrogen gas and the cyclohexanone dimer to a temperature of from 150 to 250° C., such as 150, 155, 160, 165, 170, 175, 180, 185, 190, 195, 200, 205, 210, 215, 220, 225, 230, 235, 240, 245, 250° C., while controlling a pressure within a range of 5 to 80 bars, such as 5, 10, 15, 20, 25, 30, 35, 40, 45, 50, 55, 60, 65, 70, 75, 80 bars, prior to being fed into the continuous reactor.

In the preparation method of the present disclosure, a mixing tank is further included, and disposed upstream to the continuous reactor to mix the cyclohexanone and hydrogen gas thoroughly. Wherein the mixing tank is a continuous device having an agitator and an electric heating device. In one embodiment, the mixing tank is operated at a temperature of from 150 to 250° C., such as 150, 155, 160, 165, 170, 175, 180, 185, 190, 195, 200, 205, 210, 215, 220, 225, 230, 235, 240, 245, 250° C., and under a pressure of 5 to 80 bars, such as 5, 10, 15, 20, 25, 30, 35, 40, 45, 50, 55, 60, 65, 70, 75, 80 bars.

In a batch process, the reactor is a batch reactor operated in such a mode that the reactor is loaded in batches to perform the reaction and unloaded when the reaction is completed or performed for a predetermined period. In the examples of the present disclosure, the batch reactor further includes an agitator device and therefore the reactor is a stirred tank reactor, and the agitator device rotates at a speed of 250 to 500 rpm. Wherein the agitator device can be selected from paddle agitator, turbine agitator, blade agitator, anchor agitator, folding blade agitator, side agitator, propeller agitator, magnetic heating agitator, or helical ribbon agitator.

In one embodiment, when the reactor is a batch reactor, the mass ratio of the catalyst to the cyclohexanone dimer is from 2 to 20%, such as 2, 4, 6, 8, 10, 12, 14, 16, 18, or 20%.

In another embodiment, when the reactor is a batch reactor, the hydrogenation is performed at a temperature of 150 to 250° C., such as 150, 155, 160, 165, 170, 175, 180, 185, 190, 195, 200, 205, 210, 215, 220, 225, 230, 235, 240, 245, 250° C.

In still another embodiment, when the reactor is a batch reactor, the hydrogenation is performed for 4 to 8 hrs, such as 4, 5, 6, 7, or 8 hrs.

In addition, the method of the present disclosure can further includes separating the 2-cyclohexyl cyclohexanol from hydrogen gas and byproducts with a separation unit downstream to the reactor; in one embodiment, the separation unit comprises a gas-liquid separator to separate 2-cyclohexyl cyclohexanol from hydrogen gas; and a plurality of distillation devices for isolating other byproducts and for refluxing unconverted cyclohexanone dimer to the reactor. The separation unit is not limited to that described above.

The features and effects of the present disclosure are described in detail through Examples which are not construed as limiting the scope of the present disclosure.

The conversion rates and selectivity recorded in the specification are defined as following:

$$\text{Conversion rate} = \frac{\text{(Initial Concentration of cyclohexanone dimer)} - \text{(Residual concentration of cyclohexanone dimer)}}{\text{Initial Concentration of cyclohexanone dimer}} \times 100\%$$

$$\text{Selectivity} = \frac{\text{Concentration of 2-cyclohexyl cyclohexanol in product}}{\text{Consumed concentration of cyclohexanone dimer}} \times 100\%$$

EXAMPLES

Preparation Example 1: Preparation of Catalyst 1.3 g hexachloroplatinic acid was dissolved in 100 g deionized water, 100 g γ-alumina was added to the aforementioned aqueous solution of metal salts, and oven dried at 110° C. to remove water. A catalyst was calcined at 450° C. for 8 hrs, and reduced under a hydrogen atmosphere at 320° C. for 8 hrs to obtain the needed catalyst having an inert carrier of alumina and an active metal Pt content of 0.1 wt %.

Preparation Example 2: Preparation of Catalyst 5.8 g ruthenium trichloride was dissolved in 100 g deionized water, 100 g γ-alumina was added to the aforementioned aqueous solution of metal salts, and oven drying at 110° C. to remove water. A catalyst was calcined at 450° C. for 8 hrs, and reduced under a hydrogen atmosphere at 320° C. for 8 hrs to obtain the needed catalyst having an inert carrier of alumina and an active metal Ru content of 2 wt %.

Preparation Example 3: Preparation of Catalyst 26 g nickel nitrate was dissolved in 100 g deionized water, 100 g silicon dioxide was added to the aforementioned aqueous solution of metal salts, and oven drying at 110° C. to remove water. A catalyst was calcined at 450° C. for 8 hrs and reduced under a hydrogen atmosphere at 320° C. for 8 hrs to obtain the needed catalyst having an inert carrier of alumina and an active metal Ni content of 5 wt %.

Preparation Example 4: Preparation of Catalyst 25.5 g cobalt nitrate was dissolved in 100 g deionized water, 100 g silicon dioxide was added to the aforementioned aqueous solution of metal salts, and oven drying at 110° C. to remove water. A catalyst was calcined at 450° C. for 8 hrs and reduced under a hydrogen atmosphere at 320° C. for 8 hrs to obtain the needed catalyst having an inert carrier of alumina and an active metal Co content of 5 wt %.

Example 1

60 g catalyst of above Preparation Example 1 in the form of granules was taken and filled in a fixed bed reactor, 2-(1-cyclohexenyl)cyclohexanone and hydrogen gas were fed into the reactor under controlled flow rates, and a continuous hydrogenation was performed by controlling the reactor at a temperature of 180° C. and a pressure of 15 kg/cm$^2$, to prepare 2-cylcohexyl cyclohexanol as product; wherein the weight hourly space velocity of the 2-(1-cyclohexenyl)cyclohexanone was 0.2 hr$^{-1}$, and the ratio of hydrogen to oil was 12.1. A stable reaction was achieved after reacting for 8 hrs, the product was analyzed through a Shimadzu GC-2010 Plus gas chromatography, and the conversion rate and selectivity are recorded in Table 1.

Example 2

The same preparation method as Example 1 was performed to prepare 2-cyclohexyl cyclohexanol as product, except that the catalyst was replaced with a catalyst having carbon (C) as the inert carrier and an active metal palladium (Pd) content of 1 wt % (purchased from N.E CHEMCAT), and the conversion rate and selectivity are recorded in Table 1.

Examples 3 to 5

The same preparation methods as Example 1 were performed to prepare 2-cyclohexyl cyclohexanol as products, except that the catalysts were replaced with the catalysts of Preparation Examples 2 to 4, respectively, and the conversion rates and selectivity are recorded in Table 1.

Examples 6 and 7

The same preparation method as Example 1 was performed to prepare 2-cyclohexyl cyclohexanol as products, except that the ratios of hydrogen to oil were replaced as shown in Table 2, respectively, and the conversion rates and selectivity are recorded in Table 2.

Example 8 to 10

The same preparation method as Example 1 was performed to prepare 2-cyclohexyl cyclohexanol as products, except that the weight hourly space velocities (WHSVs) were replaced as shown in Table 3, respectively, and the conversion rates and selectivity are recorded in Table 3.

Example 11

10 g catalyst of above Preparation Example 1 was taken and filled in a tank reactor having a volume of 1 L and equipped with a blade agitator, a batch hydrogenation was performed by controlling the reactor at a temperature of 210° C. and under a pressure of 5 kg/cm$^2$, to prepare 2-cyclohexyl cyclohexanol as product; wherein the ratio of hydrogen to oil was 12.1, the mass ratio of the catalyst and the cyclohexanone dimer was 10%, and the rotation speed of the agitator was 300 rpm. A stable reaction was achieved after reacting for 5 hrs, the product was analyzed through a Shimadzu GC-2010 Plus gas chromatography, and the conversion rate and selectivity are recorded in Table 4.

Examples 12 to 16

The same preparation method as Example 11 was performed to prepare 4-cyclohexyl cyclohexanol as products, except that the temperature and pressure conditions of the reactor were replaced as shown in Table 4, respectively, and the conversion rates and selectivity are recorded in Table 4.

TABLE 1

| | Catalyst | | | Continuous Reaction Conditions | | | | |
|---|---|---|---|---|---|---|---|---|
| | Active Metal | Carrier | Active Metal Content (%) | Pressure (kg/cm$^2$) | Temperature (° C.) | Ratio of hydrogen to oil | Conversion rate (%) | Selectivity (%) |
| Ex. 1 | Pt | Al$_2$O$_3$ | 0.1 | 15 | 180 | 12.1 | 100 | 91.7 |
| Ex. 2 | Pd | C | 1 | | | | 84.05 | 28.06 |
| Ex. 3 | Ru | Al$_2$O$_3$ | 2 | | | | 89.75 | 36.97 |
| Ex. 4 | Ni | SiO$_2$ | 5 | | | | 99.49 | 77.32 |
| Ex. 5 | Co | SiO$_2$ | 5 | | | | 99.94 | 95.38 |

TABLE 2

| | Catalyst | | | Continuous Reaction Conditions | | | | |
|---|---|---|---|---|---|---|---|---|
| | Active Metal | Carrier | Active Metal Content (%) | Pressure (kg/cm$^2$) | Temperature (° C.) | Ratio of hydrogen to oil | Conversion rate (%) | Selectivity (%) |
| Ex. 1 | Pt | Al$_2$O$_3$ | 0.1 | 15 | 180 | 12.1 | 100 | 91.7 |
| Ex. 6 | | | | | | 5 | 100 | 81.6 |
| Ex. 7 | | | | | | 18.2 | 100 | 91.5 |

TABLE 3

| | Catalyst | | | Continuous Reaction Conditions | | | | |
|---|---|---|---|---|---|---|---|---|
| | Active Metal | Carrier | Active Metal Content (%) | Pressure (kg/cm$^2$) | Temperature (° C.) | Weight Hourly Space Velocity (hr$^{-1}$) | Conversion rate (%) | Selectivity (%) |
| Ex. 1 | Pt | Al$_2$O$_3$ | 0.1 | 15 | 180 | 0.2 | 100 | 91.7 |
| Ex. 8 | | | | | | 2 | 54.2 | 36.7 |
| Ex. 9 | | | | | | 4 | 29.4 | 33.1 |
| Ex. 10 | | | | | | 8 | 23.3 | 32.1 |

TABLE 4

| | Catalyst | | | Batch Reaction Conditions | | | | |
|---|---|---|---|---|---|---|---|---|
| | Active Metal | Carrier | Active Metal Content (%) | Pressure (kg/cm$^2$) | Temperature (° C.) | Ratio of hydrogen to oil | Conversion rate (%) | Selectivity (%) |
| Ex. 11 | Pt | Al$_2$O$_3$ | 0.1 | 5 | 210 | 12.1 | 95.75 | 91.7 |
| Ex. 12 | | | | 15 | 180 | | 100 | 91.7 |
| Ex. 13 | | | | 20 | 170 | | 100 | 91.32 |
| Ex. 14 | | | | 25 | 190 | | 100 | 79.68 |
| Ex. 15 | | | | 50 | 150 | | 100 | 70.5 |
| Ex. 16 | | | | 15 | 250 | | 99.94 | 6.56 |

In conclusion, the method for preparing 2-cyclohexyl cyclohexanol described by the present disclosure is performed through hydrogenation of the cyclohexanone dimer at a particular range of temperature and pressure in the presence of a catalyst, to prepare 2-cyclohexyl cyclohexanol with a yield effectively improved by 50% or more. Moreover, the resultant product needs no separation through a complex purification procedure, since the preparation process has the nature of high conversion rate and selectivity. The preparation cost is thus reduced, and the method has the value of the industrial application.

The above examples are used for illustration only, but not for limiting the present disclosure. Modifications and alternations can be made to above examples by any one skilled in the art, without departing from the spirit and scope of the present disclosure. Therefore, the range claimed by the present disclosure should be defined by attached Claims, and should be encompassed within the disclosure of the present disclosure as long as it doesn't influence effects and purposes of the present disclosure.

What is claimed is:

1. A method for preparing 2-cyclohexyl cyclohexanol, comprising:

hydrogenating a cyclohexanone dimer of Formula (I) with hydrogen gas at a temperature ranging from 150° C. to 250° C. in a reactor containing a catalyst to prepare the 2-cyclohexyl cyclohexanol,

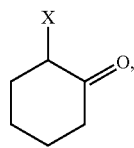

(I)

wherein X is cyclohexyl, cyclohexylidene, cyclohexenyl or unsubstituted phenyl, and wherein a molar ratio of the hydrogen gas to the cyclohexanone dimer of Formula (I) ranges from 1 to 25.

2. The method of claim 1, wherein the cyclohexanone dimer of Formula (I) is one obtained by self-condensation of cyclohexanone.

3. The method of claim 1, wherein the cyclohexanone dimer of Formula (I) is 2-(1-cyclohexenyl)cyclohexanone.

4. The method of claim 1, wherein the catalyst comprises an active metal and a carrier, and wherein the active metal is at least one element selected from Group VIIIB metals.

5. The method of claim 4, wherein the carrier is at least one element selected from the group consisting of alumina, silica and carbon.

6. The method of claim 4, wherein the active metal comprises 0.1 to 10 wt % of a weight of the catalyst.

7. The method of claim 1, wherein the cyclohexanone dimer of Formula (I) is subjected to hydrogenating under a pressure of 5 to 80 bars.

8. The method of claim 1, wherein the reactor is a continuous reactor.

9. The method of claim 8, wherein the continuous reactor is a fixed bed reactor.

10. The method of claim 9, wherein a weight hourly space velocity of the cyclohexanone dimer is from 0.1 to 10 $hr^{-1}$.

11. The method of claim 9, wherein the cyclohexanone dimer flows in a same direction as the hydrogen gas in the fixed bed reactor.

12. The method of claim 8, further comprising, prior to feeding into the continuous reactor, heating the hydrogen gas and the cyclohexanone dimer to a temperature of from 150° C. to 250° C. and controlling a pressure at from 5 to 80 bars.

13. The method of claim 8, further comprising, prior to performing hydrogenating, mixing cyclohexanone with the hydrogen gas in a mixing tank upstream to the continuous reactor.

14. The method of claim 13, wherein the mixing tank is at a temperature of from 150° C. to 250° C. and under a pressure of 5 to 80 bars.

15. The method of claim 1, wherein the reactor is a batch reactor.

16. The method of claim 15, wherein a mass ratio of the catalyst to the cyclohexanone dimer is 2% to 20%.

17. The method of claim 15, wherein the hydrogenating is performed for 4 to 8 hrs.

18. The method of claim 1, further comprising separating the 2-cyclohexyl cyclohexanol from the hydrogen gas and byproducts with a separation unit downstream to the reactor.

* * * * *